United States Patent [19]

Niwa et al.

[11] 4,313,810
[45] Feb. 2, 1982

[54] OXYGEN CONCENTRATION SENSING APPARATUS

[75] Inventors: Hitoshi Niwa, Anjo; Naoto Miwa, Tsushima; Masatoshi Suzuki, Kariya; Masami Ouki, Nagoya, all of Japan

[73] Assignee: Nippondenso Co., Ltd., Kariya, Japan

[21] Appl. No.: 53,181

[22] Filed: Jun. 27, 1979

[30] Foreign Application Priority Data

Jul. 7, 1978 [JP] Japan .................................. 53/83343

[51] Int. Cl.³ .......................................... G01N 27/58
[52] U.S. Cl. ................................ 204/195 S; 60/276; 123/489
[58] Field of Search ........................... 204/195 S, 1 S; 123/489; 60/276

[56] References Cited

U.S. PATENT DOCUMENTS 4,207,159  6/1980  Kimura et al. .................. 204/195 S Primary Examiner—G. L. Kaplan
Attorney, Agent, or Firm—Cushman, Darby & Cushman

[57] ABSTRACT

An oxygen concentration sensing apparatus in which a block of an oxygen-ion conductive solid electrolyte is interposed between a first electrode and a second electrode disposed opposite to each other. The first electrode is made of a catalytic metal and is exposed at a portion thereof on a surface of the solid electrolyte block, and an electrical insulating heat-resistive layer having a plurality of communication pores covers the exposed portion of the first electrode. The second electrode is porous and made of a catalytic metal. The solid electrolyte is wholly exposed to a stream of gases containing oxygen whose concentration is to be measured, and during measurement, a current source supplies continuously an electric current in a direction from the first electrode toward the second electrode. When the partial pressure of oxygen gas produced at the first electrode and existing in the vicinity thereof exceeds a predetermined value, the excess pressure portion of oxygen gas is discharged into the stream of gases through the communication pores of the heat-resistive layer thereby maintaining substantially constant the partial pressure of oxygen gas in the vicinity of the first electrode. An electromotive force representing the ratio between the partial pressure of oxygen around the first electrode and that in the stream of gases containing oxygen is measured to determine the concentration of oxygen contained in the gases.

5 Claims, 7 Drawing Figures

OXYGEN CONCENTRATION SENSING APPARATUS

BACKGROUND OF THE INVENTION

This invention relates to an oxygen concentration sensing apparatus conveniently usable for sensing the concentration of oxygen in gases, for example, exhaust gases from internal combustion engines for automotive vehicles.

SUMMARY OF THE INVENTION

It is a primary object of the present invention to provide an improved oxygen concentration sensing apparatus of simplified construction comprising a block or a mass of a solid electrolyte for sensing the concentration of oxygen in gases, for example, exhaust gases from internal combustion engines for automotive vehicles, which eliminates the necessity for exposing a portion of the solid electrolyte block to the atmoshpere which is a reference gas, and which eliminates also the gastight sealing means required hitherto for preventing direct communication between the atmosphere and the stream of gases containing oxygen whose concentration is to be measured.

In accordance with the present invention there is provided an oxygen concentration sensing apparatus comprising a block of an oxygen-ion conductive solid electrolyte exposed wholly to a stream of gases containing oxygen whose concentration is to be measured, a first electrode and a second electrode disposed opposite to each other the solid electrolyte block interposed therebetween, the first electrode being made of a catalytic metal capable of exerting a catalytic action on gases containing oxygen and being exposed at least a portion thereof on one of the faces of the solid electrolyte block to be covered at its exposed portion with a layer of an electrical insulating heat-resistive material having a plurality of communication pores, the second electrode being porous and made of a catalytic metal capable of exerting a catalytic action on gases containing oxygen, and an electric circuit supplying continuously an electric current in a direction of from the first electrode toward the second electrode during the period of measurement of the oxygen concentration. In the apparatus of the present invention having the features above described, the solid electrolyte block is wholly exposed to the stream of gases containing oxygen whose concentration is to be measured, and the current supplied continuously from the electric circuit to flow from the first electrode toward the second electrode during measurement acts to turn oxygen in the stream of gases into oxygen ions at the interface between the second electrode and the solid electrolyte block. The oxygen ions migrate through the interior of the solid electrolyte block to be turned into the gaseous form again at the first electrode. When the partial pressure of oxygen gas produced at and existing in the vicinity of the first electrode exceeds a predetermined value, the excess pressure portion of oxygen gas is discharged into the stream of gases through the communication pores in the electrical insulating heat-resistive material layer, thereby maintaining substantially constant the partial pressure of oxygen gas existing in the vicinity of the first electrode. Consequently, an oxygen gas existing in the vicinity of the first electrode and the parital pressure of oxygen gas existing in the stream of gases subjected to the measurement, and on the basis of the generated electromotive force, the oxygen concentration in the gases can be determined. Therefore, the present invention eliminates the prior art necessity for exposing a portion of the solid electrolyte block to the atmosphere which is the reference gas used for the measurement of the oxygen concentration. The present invention which eliminates the above requirement is therefore advantageous in that the gastight sealing arrangement required hitherto for preventing direct communication between the atmosphere and the stream of gases subjected to the oxygen concentration measurement is entirely unnecessary, and the construction of the apparatus can be greatly simplified.

The elimination of the prior art necessity for the provision of the gastight sealing arrangement for preventing direct communication between the atmosphere and the stream of gases subjected to the oxygen concentration measurement provides such an additional advantage that the solid electrolyte block of complex shape and large size heretofore required for ensuring the gastight seal is entirely unnecessary.

In the present invention, the solid electrolyte block can be bodily exposed to the stream of gases subjected to the oxygen concentration measurement, so that any appreciable temperature differences do not appear among any parts of the solid electrolyte block. This provides such other advantages that the thermal-shock resistivity of the solid electrolyte block is improved, and the thermal response characteristic of the solid electrolyte block is also improved due to the fact that the solid electrolyte block is quickly heated up to its operating temperature.

In the present invention, the current from the current source is continously supplied to flow from the first electrode toward the second electrode during measurement, and the partial pressure of oxygen gas existing in the vicinity of the first electrode is always stable or maintained substantially constant throughout the period of measurement. This provides such another advantage that a stable electromotive force can be generated to insure accurate measurement of the concentration of oxygen contained in the stream of gases subjected to the oxygen concentration measurement.

DESCRIPTION OF THE PREFERRED EMBODIMENTS

Preferred embodiment of the oxygen concentration sensing apparatus according to the present invention will now be described with reference to the drawings.

Figure 1:
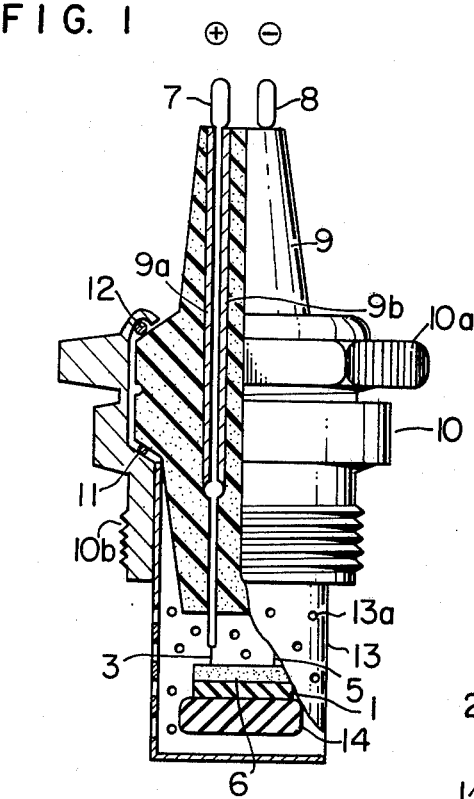
FIG. 1 is a front elevational view, partly in section, of a first embodiment of the oxygen concentration sensing apparatus according to the present invention.
Figure 2:
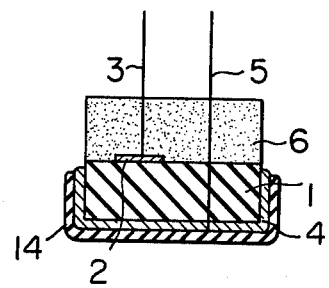
FIG. 2 is a schematic sectional view showing the detailed structure of the solid electrolyte block and associated parts shown in FIG. 1.

Referring to FIGS. 1 and 2 showing a first embodiment of the present invention, the apparatus comprises a block of an oxygen-ion conductive solid electrolyte 1 having a shape of a rectangular parallelepiped. This solid electrolyte block 1 is obtained by mixing suitable amounts of $ZrO_2$ and $Y_2O_3$, and firing the mixture at a high temperature of about 1,500° C. to 1,700° C. to render it into the form of a solid solution. This solid electrolyte block 1 has an internal resistance lower than 1 MΩ at the room temperature. A porous first electrode 2 made of a catalytic metal such as platinum is provided on a face or surface of the solid electrolyte block 1. This first electrode 2 is formed by coating a paste containing platinum on that face of the solid electrolyte block 1 and then firing to deposit platinum in porous form. A lead wire 3 made of a metal such as platinum is electrically connected at one end thereof to the first electrode 2. The connected end portion of the lead wire 3 may be bent into an L-like shape so as to increase the contact area between the electrode 2 and the lead wire 3.

A second electrode 4 in the form of a thin porous conductive film of a catalytic metal such as platinum is provided on the solid electrolyte block 1 to extend over the remaining five faces of the solid electrolyte block 1 and is electrically connected to one end of another lead wire 5 made of a metal such as platinum. This second electrode 4 is formed by, for example, a chemical plating technique. A layer of an electrical insulating heat-resistive material 6 such as aluminum oxide having a plurality of communication pores or pores which pass gas such as air is securely fixed or bonded by an inorganic heat-resistive adhesive to the face of the solid electrolyte block 1 having the first electrode 2 thereon, so that the first electrode 2 is entirely covered by the layer 6. A porous protective layer 14 of a material such as magnesia-alumina spinel covers the outer surface of the second electrode 4. Terminal rods 7 and 8 made of a conductive metal such as nickel are inserted in individual elongate holes 9a extending through a cylindrical insulator 9 made of a heat-resistive non-conductive material having a high mechanical strength such as alumina porcelain. Each of these terminal rods 7 and 8 is inserted in a large-diameter portion of the associated elongate hole 9a and is securely held gastight in that hole portion by a heat-resistive glass material 9b which is fused to solidify to fill the gap between the terminal rod 7, 8 and the inner wall of the hole 9a.

The lead wires 3 and 5 connected at one end thereof to the respective electrodes 2 and 4 on the solid electrolyte block 1 extend through the small-diameter portion of the holes 9a to be welded or otherwise fixed at the other end thereof to the inner end of the terminal rods 7 and 8 respectively to establish electrical connections between the electrodes 2, 4 and the assoiated terminal rods 7, 8. The insulator 9 is supported at its middle portion within a hollow cylindrical housing 10 made of a heat-resistive corrosion-resistive metal, with an annular metal packing 11 and a caulking ring 12 interposed therebetween. The insulator 9 and the housing 10 are tightly fixed together by caulking the caulking ring 12 under heat to the area of the housing 10 opposite to the caulking ring 12.

The housing 10 is formed with a hexagon nut portion 10a and an externally threaded portion 10b. A cylindrical protective cover 13 made of a heat-resistive corrosion-resistive metal having a closed bottom and having a multiplicity of perforations 13a in its side wall is tightly fixed at its upper end portion to the inner wall of the threaded portion 10b of the housing 10 as by welding so as to completely enclose the solid electrolyte block 1 thereinside. The housing 10 is fixedly mounted at its externally threaded portion 10b in an exhaust pipe (not shown) of an internal combustion engine of an automotive vehicle in such a relation that the entirety of the solid electrolyte block 1 is exposed to the stream of exhaust gases flowing through the exhaust pipe.

Figure 3:
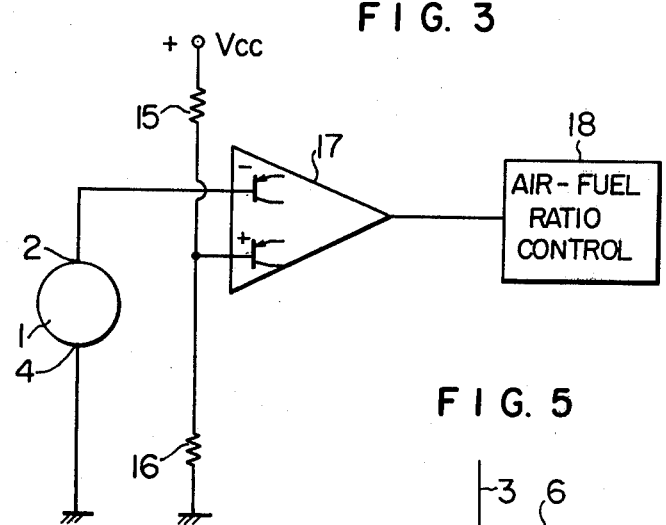
FIG. 3 is a connection diagram of an electric circuit for supplying an electric current across the electrodes 2 and 4 shown in FIG. 1.

FIG. 3 is a connection diagram of an electric circuit for supplying an electric current across the electrodes 2 and 4 in the oxygen concentration sensing apparatus having the construction above described. Referring to FIG. 3, resistors 15 and 16 are connected across ground and a power supply terminal supplying a predetermined constant power supply voltage $V_{cc}$, so that a reference voltage of, for example, 0.45 volts corresponding to the stoichiometric air-fuel ratio can be applied to a comparator 17. This comparator 17 is of such a type that it supplies continuously a constant current of, for example, 200 μA in a direction from the first electrode 2 toward the second electrode 4 on the solid electrolyte block 1 during measurement of the concentration of oxygen in engine exhaust gases. The comparator 17 compares the electromotive force generated from the solid electrolyte block 1 with the reference voltage of 0.45 volts indicative of the stoichiometric air-fuel ratio, and an output signal indicative of whether the air-fuel ratio of engine exhaust gases is richer or leaner than the stoichiometric air-fuel ratio is applied from the comparator 17 to an air-fuel ratio control circuit 18. This control circuit 18 controls the air-fuel ratio on the basis of the output of the comparator 17.

The operation of the oxygen concentration sensing apparatus of the present invention having the aforementioned construction will now be described. During measurement of the concentration of oxygen in the engine exhaust gases, current is continuously supplied from the electric circuit including the comparator 17 to flow from the first electrode toward the second electrode 4 on the solid electrolyte block 1. Residual oxygen in the exhaust gases is turned into oxygen ions by the reaction $O_2 + 4e^- \rightarrow 2O^{2-}$ occurring at the interface between the second electrode 4 and the solid electrolyte block 1, and the oxygen ions thus produced migrate through the solid electrolyte block 1 toward the first electrode 2 at which the oxygen ions are turned into gaseous oxygen again by the reaction $2O^{2-} \rightarrow O_2 + 4e^-$. The first electrode 2 is bodily covered with the heat-resistive layer 6 of aluminum oxide having a plurality of communication pores as described hereinbefore. Therefore, when the partial pressure of oxygen gas produced at the first electrode 2 and existing in the vicinity thereof exceeds the partial pressure of oxygen in the exhaust gases flowing around the solid electrolyte block 1, the excess pressure portion of oxygen gas flows through the communication pores of the heat-resistive layer 6 to be discharged into the stream of exhaust gases so that the partial pressure of oxygen gas in the vicinity of the first electrode 2 is substantially maintained constant throughout the period of measurement. Thus, when the concentration of residual oxygen in the exhaust gases is low, that is, when the air-fuel ratio of the exhaust gases is richer than the stoichiometric air-fuel ratio, the ratio between the partial pressure of oxygen gas around the first electrode 2 and that around the second electrode 4 is large, and the comparator 17 provides an output V of corresponding high level. On the other hand, when the concentration of residual oxygen in the exhaust gases is high, that is, when the air-fuel ratio of the exhaust gases is leaner than the stoichiometric air-fuel ratio, the ratio between the partial pressure of oxygen gas around the first electrode 2 and that around the second electrode 4 is small, and the comparator 17 provides an output V of corresponding low level. The electromotive force E thus generated is a function of the oxygen partial pressure ratio, as follows:

$$E=(RT/4F)\cdot\log(P_1O_2/P_2O_2)$$

where $P_1O_2$ is the reference partial pressure of oxygen, that is, the partial pressure of oxygen around the first electrode 2 which is positive relative to the second electrode 4; $P_2O_2$ is the partial pressure of oxygen in the exhaust gases, that is, the partial pressure of oxygen around the second electrode 4 which is negative relative to the first electrode 2; T is the absolute temperature; and R and F are constants.

Figure 4:
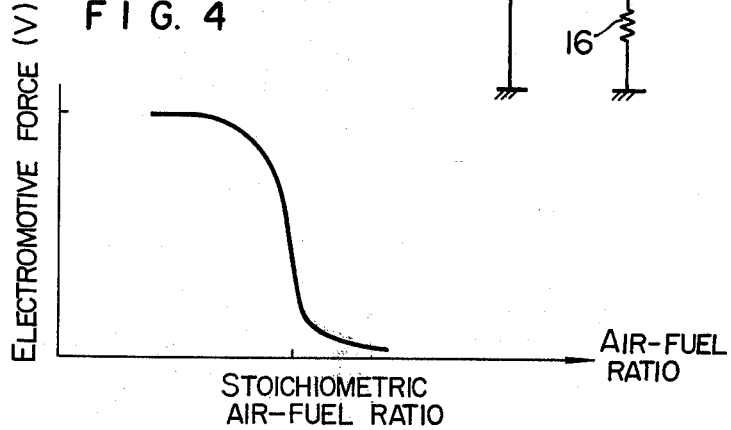
FIG. 4 is a graph illustrating the operating characteristic of the apparatus according to the present invention.

FIG. 4 shows the relation between the air-fuel ratio of exhaust gases and the electromotive force in the first embodiment of the present invention.

Figure 5:
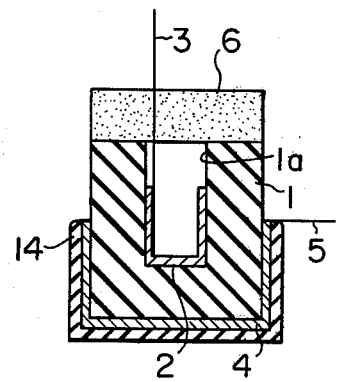
FIGS. 5 to 7 are schematic sectional views of parts of other embodiments of the present invention.

FIG. 5 shows a second embodiment of the present invention or a modification of the arrangement shown in FIG. 2. Referring to FIG. 5, a recess 1a is formed in the solid electrolyte block 1, and a paste containing platinum is coated on the wall of the recess 1a and is then fired to provide the first electrode 2. The heat-resistive layer 6 of aluminum oxide having the plural communication pores is then bonded to the solid electrolyte block 1 to cover the opening of the recess 1a.

Figure 6:
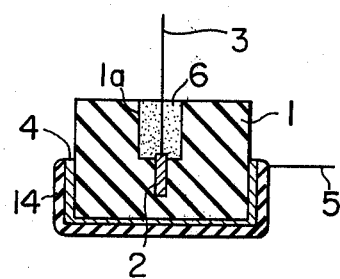

FIG. 6 shows a third embodiment of the present invention or another modification of the arrangement shown in FIG. 2. Referring to FIG. 6, a recess 1a is formed in the solid electrolyte block 1, and the platinum electrode 2 is firmly embedded in the solid electrolyte block 1 with a portion thereof exposed within the recess 1a. The heat-resistive layer 6 of aluminum oxide having the plural communication pores is then filled within and bonded to the wall of the recess 1a.

Figure 7:
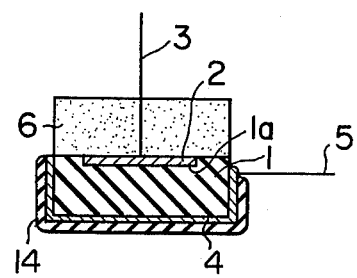

FIG. 7 shows a fourth embodiment of the present invention or a further modification of the arrangement shown in FIG. 2. FIG. 7 differs from FIG. 2 in the location of the lead-out position of the lead wire 5.

While preferred embodiments of the present invention have been described by way of example, the present invention is in no way limited to such specific embodiments, and various changes and modifications may be made therein, as follows:

(1) The material of the heat-resistive layer 6 is not limited to aluminum oxide, and any other suitable heat-resistive metal oxide such as zirconium oxide may be employed in lieu thereof. Further, powders of such a heat-resistive metal oxide may be sintered to provide the heat-resistive layer 6.

(2) The material of the electrode 2 and 4 as well as that of the lead wires 3 and 5 is not limited to platinum, and an alloy of platinum and rhodium or an alloy of platinum and palladium may be employed in lieu thereof, or rhodium or palladium may be singly employed as the material of the above elements.

(3) Besides the mixture of $Y_2O_3$ and $ZrO_2$, a mixture of CaO and $ZrO_2$ or the like may be employed to form the solid electrolyte block 1. Further, the solid electrolyte block 1 may have any other suitable shape such as a cubic or columnar shape.

(4) The lead wire 5 may be electrically connected to the housing 10.

(5) In lieu of the comparator 17 illustrated in FIG. 3, any other suitable elements such as resistors and transistors may be employed to provide flow of current from the first electrode 2 toward the second electrode 4.

(6) The first electrode 2 may be in the form of a strip of a catalytic metal instead of being formed by firing the paste.

(7) The apparatus according to the present invention is in no way limited to the application for sensing the concentration of oxygen in exhaust gases from an internal combustion engine of an automotive vehicle and finds various other useful applications.

(8) The number of communication pores in the heat-resistive layer 6 may be only one.

We claim:

1. An oxygen concentration sensing apparatus comprising:

a block of an oxygen-ion conductive solid electrolyte for exposure wholly to a stream of gases containing oxygen whose concentration is to be measured, a first electrode and a second electrode disposed opposite to each other with said solid electrolyte block interposed therebetween, said first electrode being made of a catalytic metal capable of exerting a catalytic action on gases containing oxygen, at least a portion of said first electrode being exposed on one of the faces of said solid electrolyte block, said second electrode being porous and made of a catalytic metal capable of exerting a catalytic action on gases containing oxygen, cover means covering the exposed portion of said first electrode and being a layer of an electrical insulating heatresistive material having a plurality of communication pores, and an electric circuit supplying continuously an electric current in a direction from said first electrode toward said second electrode during the period of measurement of the oxygen concentration, wherein said electric circuit comprises means for generating a reference voltage, and comparator means having first and second input terminals connected respectively to said first electrode and said generating means being constructed to cause a constant current to flow into said solid electrolyte block from said first terminal of said comparator means via said first electrode.

2. An oxygen concentration sensing apparatus as claimed in claim 1, wherein a recess is formed in said solid electrolyte block, said first electrode being provided on the wall of said recess, and said electrical insulating heat-resistive layer is bonded to said solid electrolyte block to cover the opening of said recess.

3. An oxygen concentration sensing apparatus as claimed in claim 1, wherein a recess is formed in said solid electrolyte block, said first electrode being firmly embedded in said solid electrolyte block with a portion thereof exposed within said recess, and said electrical insulating heat-resistive layer is filled within and bonded to the wall of said recess.

4. An oxygen concentration sensing apparatus as claimed in claim 1, wherein said second electrode is covered with a porous protective layer, and an electrode lead wire for said second electrode is connected to the portion of said second electrode covered with said protective layer.

5. An oxygen concentration sensing apparatus as claimed in claim 1, wherein said second electrode is covered with a porous protective layer except at least a portion thereof, and an electrode lead wire for said second electrode is connected to the electrode portion not covered with said protective layer.

* * * * *